US00PP09655P

United States Patent [19]

Dehan

[11] Patent Number: Plant 9,655

[45] Date of Patent: Oct. 8, 1996

[54] ASTER PLANT NAMED 'SUNRIO'

[75] Inventor: Klara Dehan, Holon, Israel

[73] Assignee: Danziger "Dan" Flower Farm, Moshav Mishmar Hashiva, Israel

[21] Appl. No.: 471,561

[22] Filed: Jun. 6, 1995

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 9,175 6/1995 Dehan ..... Plt./68.1

*Primary Examiner*—James R. Feyrer
*Attorney, Agent, or Firm*—Foley & Lardner

[57] ABSTRACT

A new and distinct cultivar of aster plant named Sunrio, characterized by its white ray floret color; yellow-green tubular discs; tall and sturdy stems, each of which carries many flowers; excellent branching, and symmetrical, conical-shaped main and lateral stem shape.

1 Drawing Sheet

The present invention comprises a new and distinct cultivar of Aster plant, botanically known as *Astor ericoides*, hereinafter referred to by the cultivar name Sunrio.

The new cultivar was originated from a cross made in a controlled breeding program by the inventor Klara Dehan in Mishmar Hashiva, Israel.

Both the female, or seed, and the male, or pollen parents were cultivars of *Aster ericoides* which are unknown at this time. Both parents are proprietary lines used exclusively for breeding.

Sunrio was discovered and selected by the inventor as a flowering plant within the progency of the stated cross in a controlled environment in Mishmar Hashiva, Israel. Asexual reproduction of the new cultivar by leaf cuttings peforming by the inventor at Mishmar Hashiva, Israel has demonstrated that the combination of characteristics as herein disclosed for the new cultivar are firmly fixed and retained through successive generations of asexual reproduction.

Sunrio has not been observed under all possible environmental conditions. The phenotype may vary somewhat with variations in environment such as temperatures, light intensity and daylength, without, however, any variation in genotype. The following observations, measurements and values describe the new cultivar as grown in Mishmar Hashiva, Israel under conditions which closely approximate those generally used in commercial practice.

The following traits have been repeatedly observed and are determined to be basic characteristics of Sunrio which in combination distinguish this aster as a new and distinct cultivar:

1. Medium size, white flowers.
2. Yellow-green tubular disc florets.
3. Tall and sturdy stems, each of which carries many flowers.
4. Excellent branching.
5. Lateral flower stems near bottom of main stem are substantially longer than laterals near top, therefore forming a symmetric conical stem shape.

The new cultivar can be compared to the aster Sunsol. Similar characteristics are flower size, long stems, and good branching. Sunrio is distinguished from Sunsol by its yellow-green tubular disc florets, and its larger and more glossy foliage.

The accompanying color photographic drawing illustrates a portion of a typical specimen plant of the new cultivar, with partially open and completely open flowers being illustrated.

In the following description, color references are made to

The Royal Horitcultural Society Colour Chart (R.H.S.), except where general colors of ordinary significance are referred to. Color values were taken in the morning in Mishmar Hashiva, Israel.

Classification:

*Botanical.*—*Aster ericoides* Hybrid cv. Sunrio.

*Commercial.*—Daisy-like spray or garden variety.

Parentage:

*Male parent.*—Unknown seedling of *Aster ericoides.*

*Female parent.*—Unknown seedling of *Aster ericoides.*

Propagation: The new cultivar holds its distinguishing characteristics through successive propagations by leaf cuttings.

INFLORESCENCE

A. Capitulum:
- *Form.*—Daisy, round, generally flat.
- *Type.*—Semi-double, with 1.5 rows of petals.
- *Diameter across face.*—25–30 mm.

B. Corolla of ray florets:
- *Color (general tonality from a distance of three meters).*—White.
- *Color (upper surface).*—White 155D.
- *Color (under surface).*—White 155D.
- *Shape.*—Florets are generally narrow and oblong, with apex rounded; slightly concave.

C. Corolla of disc florets:
- *Color (mature).*—1B.
- *Color (immature).*—1A.
- *Diameter of disc.*—9 mm.

D. Flowering period: When field grown in natural season, plants planted in June will flower in September. In winter greenhouse production, preferred culture includes approximately four weeks of long-day treatment after pinching until the stems elongate to approximately 10 cm, followed by short days. From the start of short days, flowering occurs in approximately 7 weeks in the fall and 9 weeks in the winter.

E. Reproductive organs:
- *Androecium.*—Stamens present on both ray and disc florets and yellow-green in color; pollen is yellow and found only in the winter season in Israel.
- *Gynoecium.*—Present on disc florets; green in color.

PLANT

A. General appearance: Excellent branching and tall stems result in a great abundance of medium size white flowers; height of main stem reaches 95–100 cm.

B. Foliage:

*Color.*—147A.

*Shape.*—Linear, with occasional downward reflexing at the tip.

*Size.*—Typical leaves at upper part of plant (80% from base) are 100 mm in length and 5 mm in width; larger leaves at bottom of plant (20% from base) are 185 mm in length and 13 mm in width.

*Margin.*—Entire.

*Arrangement.*—Alternate, with angle acute.

I claim:

1. A new and distinct cultivar of aster plant named Sunrio, as illustrated and described.

* * * * *

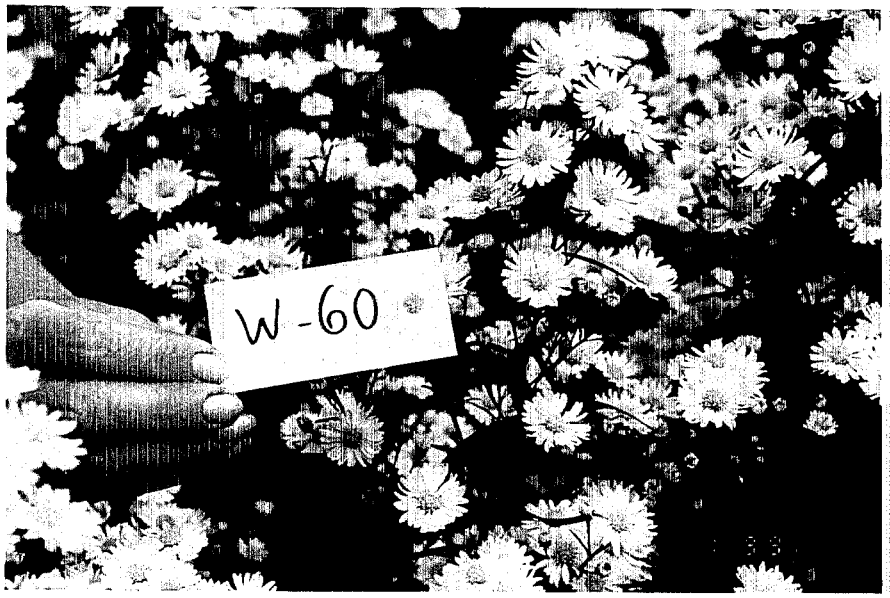
W-60